(12) United States Patent
Sayles (10) Patent No.: US 10,909,343 B1
(45) Date of Patent: Feb. 2, 2021

(54) AUTOMATED SCREW IDENTIFICATION SYSTEM AND METHOD WITH LABELED PEGS

(71) Applicant: Summate Technologies, Inc., Newburyport, MA (US)

(72) Inventor: Philip William Sayles, Newburyport, MA (US)

(73) Assignee: Summate Technologies, Inc., Newburyport, MA (US)

( * ) Notice: Subject to any disclaimer, the term of this patent is extended or adjusted under 35 U.S.C. 154(b) by 0 days.

(21) Appl. No.: 16/510,476

(22) Filed: Jul. 12, 2019

(51) Int. Cl.
  *G06K 7/10* (2006.01)
  *G06K 7/14* (2006.01)

(52) U.S. Cl.
  CPC ......... *G06K 7/1417* (2013.01); *G06K 7/1413* (2013.01)

(58) Field of Classification Search
  CPC .. G06Q 10/087; G06Q 10/08; G06Q 10/0875; G06Q 50/22; G06K 7/14; A61B 50/20; A61B 50/30; A61B 50/33
  See application file for complete search history.

(56) References Cited

U.S. PATENT DOCUMENTS

| | | |
|---|---|---|
| 3,967,202 A | 6/1976 | Batz |
| 4,614,945 A | 9/1986 | Brunius |
| 4,816,839 A | 3/1989 | Landt |
| 5,234,433 A | 8/1993 | Bert |
| 5,528,222 A | 6/1996 | Moskowitz |
| 5,641,634 A | 6/1997 | Mandecki |
| 5,682,143 A | 10/1997 | Brady |
| 5,786,626 A | 7/1998 | Brady |
| 5,825,298 A | 10/1998 | Walter |

(Continued)

FOREIGN PATENT DOCUMENTS

| | | |
|---|---|---|
| KR | 20070078826 B1 | 8/2007 |
| KR | 100875690 B1 | 12/2008 |

(Continued)

OTHER PUBLICATIONS

Axisa, F., et al., "Design and fabrication of a low cost implantable bladder pressure monitor," 2009 Annual International Conference of the IEEE Engineering in Medicine and Biology Society, pp. 4864-4867 (2009).

(Continued)

*Primary Examiner* — Thien M Le
(74) *Attorney, Agent, or Firm* — Blueshift IP, LLC; Robert Plotkin (57) ABSTRACT

A peg, suitable for insertion into a hole in a surgical tray, includes a cap piece, a directional member, and a columnar protrusion. The cap piece includes a machine-readable object that contains data representing information about one or more surgical assets. The directional member has a directional feature which points in a particular direction and which may be oriented to point to one or more surgical assets having the properties represented by the data on the machine-readable object. The columnar protrusion is suitable for being securely inserted into a hole in the surgical tray, such as by being pushed into a hole in a rubber footer. Removal of a surgical asset from the tray is performed by reading data from the machine-readable object that points to the surgical asset and using that data to modify a count of the type of object contained in the tray.

16 Claims, 9 Drawing Sheets

(56) References Cited

U.S. PATENT DOCUMENTS

| | | | |
|---|---|---|---|
| 5,874,902 A | 2/1999 | Heinrich | |
| 5,892,458 A | 4/1999 | Anderer | |
| 5,971,156 A * | 10/1999 | Slocum | H01L 21/67333 |
| | | | 206/560 |
| 5,974,078 A | 10/1999 | Tuttle | |
| 6,104,281 A | 8/2000 | Heinrich | |
| 6,147,662 A | 11/2000 | Grabau | |
| 6,177,859 B1 | 1/2001 | Tuttle | |
| 6,293,684 B1 | 9/2001 | Riblett | |
| 6,331,280 B1 * | 12/2001 | Wood | A61L 2/26 |
| | | | 206/268 |
| 6,590,150 B1 | 7/2003 | Kiefer | |
| 6,899,644 B1 * | 5/2005 | Song | A63B 57/13 |
| | | | 473/397 |
| 6,925,447 B2 | 8/2005 | McMenimen | |
| 7,053,294 B2 | 5/2006 | Tuttle | |
| 7,098,394 B2 | 8/2006 | Armer | |
| 7,135,977 B2 | 11/2006 | Burg | |
| 7,195,149 B2 | 3/2007 | Baker | |
| 7,328,837 B2 | 2/2008 | Baker | |
| 7,412,898 B1 | 8/2008 | Smith | |
| 7,585,302 B2 | 9/2009 | Revie | |
| 7,633,111 B2 | 12/2009 | Friedrich | |
| 7,698,156 B2 | 4/2010 | Martucci | |
| 7,791,481 B2 | 9/2010 | Landt | |
| 7,849,807 B2 | 12/2010 | Suzuki | |
| 7,915,517 B2 | 3/2011 | Lau | |
| 8,027,632 B2 | 9/2011 | Mazar | |
| 8,089,285 B2 | 1/2012 | Hsu | |
| 8,165,658 B2 | 4/2012 | Waynik | |
| 8,350,704 B2 | 1/2013 | Mullis | |
| 8,353,917 B2 | 1/2013 | Mandecki | |
| 8,476,689 B2 | 7/2013 | Chang | |
| 8,501,122 B2 | 8/2013 | Shirazi | |
| 8,540,468 B2 | 9/2013 | Mekid | |
| 8,552,470 B2 | 10/2013 | Chen | |
| 8,574,946 B1 | 11/2013 | Martin | |
| 8,576,050 B2 | 11/2013 | Hansen | |
| 8,587,406 B2 | 11/2013 | Maltseff | |
| 8,587,410 B2 | 11/2013 | Potyrailo | |
| 8,596,544 B2 | 12/2013 | Kang | |
| 8,616,459 B2 | 12/2013 | Sykkoe | |
| 8,624,294 B2 | 1/2014 | Kline | |
| 8,628,018 B2 | 1/2014 | Zenz | |
| 8,636,220 B2 | 1/2014 | Warther | |
| 8,660,640 B2 | 2/2014 | Markowitz | |
| 8,663,120 B2 | 3/2014 | Markowitz | |
| 8,717,430 B2 | 5/2014 | Simon | |
| 8,796,186 B2 | 8/2014 | Shirazi | |
| 8,986,012 B1 * | 3/2015 | McGee | A63H 33/08 |
| | | | 434/211 |
| 8,996,393 B2 | 3/2015 | Sobie | |
| 9,313,558 B1 | 4/2016 | Mandecki | |
| 9,361,568 B2 | 6/2016 | Butler | |
| 9,370,401 B2 | 6/2016 | Sayles | |
| 9,405,950 B2 | 8/2016 | Mats | |
| 9,418,263 B2 | 8/2016 | Butler | |
| 9,418,321 B1 | 8/2016 | Gruda | |
| 9,847,044 B1 | 12/2017 | Foster | |
| 9,964,134 B1 | 5/2018 | Tran | |
| 10,470,809 B1 | 11/2019 | Sayles | |
| 10,671,969 B2 | 6/2020 | Sayles et al. | |
| 10,702,321 B2 | 7/2020 | Sayles et al. | |
| 10,786,331 B2 | 9/2020 | Sayles et al. | |
| 2003/0146836 A1 | 8/2003 | Wood | |
| 2004/0019464 A1 | 1/2004 | Martucci | |
| 2004/0078231 A1 | 4/2004 | Wilkes | |
| 2004/0172302 A1 | 9/2004 | Martucci | |
| 2005/0102167 A1 | 5/2005 | Kapoor | |
| 2005/0125068 A1 | 6/2005 | Hozack | |
| 2006/0084934 A1 | 4/2006 | Frank | |
| 2006/0232408 A1 | 10/2006 | Nycz et al. | |
| 2007/0006887 A1 | 1/2007 | Frank | |
| 2007/0135965 A1 | 6/2007 | Nguyen | |
| 2007/0239481 A1 | 10/2007 | DiSilvestro et al. | |
| 2007/0290030 A1 | 12/2007 | Fox | |
| 2008/0003667 A1 | 1/2008 | Jones | |
| 2008/0030345 A1 | 2/2008 | Austin | |
| 2009/0146032 A1 * | 6/2009 | Bettenhausen | A61B 50/30 |
| | | | 248/220.31 |
| 2010/0106194 A1 | 4/2010 | Bonutti | |
| 2010/0248981 A1 | 9/2010 | Shirazi | |
| 2012/0234922 A1 | 9/2012 | Sample | |
| 2012/0241524 A1 | 9/2012 | Blot | |
| 2012/0316987 A1 * | 12/2012 | DeBusk | G06Q 10/08 |
| | | | 705/26.8 |
| 2012/0318863 A1 | 12/2012 | Kim | |
| 2012/0325905 A1 | 12/2012 | Kim | |
| 2014/0048900 A1 | 2/2014 | Keysar | |
| 2014/0125482 A1 | 5/2014 | Rigsby | |
| 2014/0197951 A1 | 7/2014 | Savarese | |
| 2016/0212577 A1 | 7/2016 | Dor | |
| 2016/0297639 A1 * | 10/2016 | Callaway | G05B 19/4142 |
| 2017/0098049 A1 | 4/2017 | Sweeney | |
| 2017/0235897 A1 | 8/2017 | Henderson et al. | |
| 2018/0322445 A1 | 11/2018 | Sayles | |
| 2019/0380757 A1 | 12/2019 | Sayles | |
| 2020/0008902 A1 | 1/2020 | Sayles | |

FOREIGN PATENT DOCUMENTS

| | | |
|---|---|---|
| KR | 100881986 B1 | 2/2009 |
| KR | 101019674 B1 | 3/2011 |
| KR | 20110096700 A | 8/2011 |
| KR | 200462233 Y1 | 9/2012 |
| KR | 101197088 B1 | 11/2012 |
| KR | 200475044 Y1 | 10/2014 |
| KR | 101637919 B1 | 7/2016 |
| KR | 101677943 B1 | 11/2016 |
| WO | 2016208784 A1 | 12/2016 |

OTHER PUBLICATIONS

Bazaka, K., and Jacob M.V., "Implantable devices: issues and challenges," Electron, vol. 2, pp. 1-34 (2013).

Beck, H., et al., "50th Anniversary of the first successful permanent pacemaker implantation in the United States: historical review and future directions," Am J Cardiel, vol. 106, No. 6, pp. 810-818 (2010).

Fiandra, O., "The first pacemaker implant in America," Pacing Clin Electrophysiol, vol. 11, Issue 8, pp. 1234-1238 (Aug. 1988).

Food and Drug Administration, Nov. 4, 2014, Retrieved from the Internet: URL: https://www.fda.gov/medicaldevices/.

Furman, S., "Early history of cardiac pacing and defibrillation," Indian Pacing Electrophysiology, vol. 2, No. 1, pp. 2-3 (2002).

Greatbatch, W., and Holmes, CF., "History of implantable devices," IEEE Eng Med Biol Mag, vol. 10, No. 3, pp. 38-41 (1991).

Gruda, MC., et al., "A System for Implanting Laboratory Mice with Light Activated Microtransponders," J. Am. Ass. Lab. Animal Sci., vol. 49, No. 6, pp. 826-831 (Nov. 2010).

Jiang, G. and Zhou, D.D., "Technology Advances and Challenges in Hermetic Packaging for Implantable Medical Devices," Zhou, DD and Greenbaum, ES, Implantable neural prostheses 2, Techniques and Engineering Approaches, pp. 27-62 (2010).

Johnson, J.A., "FDA regulation of medical devices," Congressional research service, Federation of American Scientists, pp. 1-33 (Jun. 25, 2012).

Kileny, P.R., et al., "Effects of preoperative electrical stimulability and historical factors on performance with multichannel cochlear implant," Ann Otol Rhinol Laryngol, vol. 100, No. 7, pp. 563-568 (1991).

Larsson, B., et al., "Lessons from the first patient with an implanted pacemaker: 1958-2001," Pacing Clin Electrophysiol, vol. 26, No. 1 Part 1, pp. 114-124 (Jan. 2003).

Magjarevic, R., and Ferek-Petric, B., "Implantable cardiac pacemakers: 50 years from the first implantation," Zdravniški vestnik, vol. 79, No. 1, pp. 55-67 (2010).

Majerus, S.J., et al., "Low-power wireless micromanometer system for acute and chronic bladder-pressure monitoring," IEEE Transactions on Biomedical Engineering, vol. 58, Issue 3, pp. 763-767 (Mar. 2011).

(56) References Cited

OTHER PUBLICATIONS

Mokwa, W., "Medical implants based on Microsystems," Measurement Science and Technology, vol. 18, pp. R47-R57 (2007).

Narasimhan, S., et al., "Implantable electronics: emerging design issues and an ultra light-weight security solution," Conf. Proc. IEEE Eng Med Biol Soc, pp. 6425-6428 (2010).

Non-Final Office Action dated Oct. 3, 2019 in U.S. Appl. No. 16/534,450 of Philip Sayles, filed Aug. 7, 2019, 9 pages.

Non-Final Rejection dated Feb. 21, 2019 in U.S. Appl. No. 16/012,652 of Philip Sayles, filed Jun. 19, 2018, 10 pages.

Notice of Allowance dated Feb. 24, 2020 for U.S. Appl. No. 16/534,450 of Philip Sayles, filed Aug. 7, 2019, 13 pages.

Notice of Allowance dated Jan. 6, 2020 in U.S. Appl. No. 15/731,214 of Philip Sayles, filed May 3, 2017, 30 pages.

Notice of Allowance dated May 28, 2019 in U.S. Appl. No. 16/012,652 of Philip Sayles, filed Jun. 19, 2018, 7 pages.

Notice of Allowance dated Sep. 5, 2019 in U.S. Appl. No. 16/012,652 of Philip Sayles, filed Jun. 19, 2018, 13 pages.

Olivo, J., et al., "Energy harvesting and remote powering for implantable biosensors," IEEE Sensors Journal, vol. 11, No. 7, pp. 1573-1586 (Jul. 2011).

Onuki, Y., et al., "A review of the biocompatibility of implantable devices: current challenges to overcome foreign body response," Journal of Diabetes Science and Technology, vol. 2, No. 6, pp. 1003-1015 (Nov. 2008).

Rajappan, K., "Permanent pacemaker implantation technique: Part II," Heart, vol. 95, No. 4, pp. 334-342 (2009).

Robinson, E.J.H., and Mandecki, M., "Distributed Decisions: New Insights From Radio-Tagged Ants," In: Ant Colonies: Behavior in Insects, Nova Science Publishers, Inc. (2010).

Shlegr, Z, and Egorov, A., "Implantable electric bladder stimulator used for neurogenic failures," Biomed Eng (NY), vol. 7, pp. 382-383 (1974).

Telemetry Group "Telemetry Standard RCC Document 106-07," Chapter 2 (Sep. 2007).

Wilson B.S., and Dorman M.F., "Cochlear implants: a remarkable past and a brilliant future," Hear Res., vol. 242, pp. 3-21 (Aug. 2008).

Wong, J. Y., et al., "Biomaterials: Principles and Practices," Boca Raton, CRC Press., pp. 281 (2012).

Zoll, P.M., "Resuscitation of the heart in ventricular standstill by external electric stimulation," The New England Journal Medicine, vol. 247, No. 20, pp. 768-771 (Nov. 13, 1952).

Non Final Rejection dated Jun. 1, 2020 for U.S. Appl. No. 16/573,584 of Philip Sayles, filed Sep. 17, 2019, 18 pages.

Notice of allowance dated Jul. 8, 2020 in U.S. Appl. No. 16/573,584 of Philip Sayles, filed Sep. 17, 2019, 12 pages.

\* cited by examiner

AUTOMATED SCREW IDENTIFICATION SYSTEM AND METHOD WITH LABELED PEGS

BACKGROUND

Modern surgical procedures involve the use of a wide variety of supplies and implants, such as screws, plates, Kirschner wires (K-wires), anchors, and drill bits. It is critical to track and create a record of the type and quantity of the supplies used both inside and outside of the field during a particular surgical procedure for a variety of reasons, such as billing, quality assurance, accurate patient records, and determining the type and quantity of supplies that need to be reordered and restocked. Creating such an accurate record while a surgery is being performed is complicated by a variety of factors, including the wide variety of supplies that are used, difficulty of tracking what is used inside the sterile field, the lack of space on the tray to print the corresponding part number of each distinct screw type, the small size of such supplies, and the difficulty of distinguishing similar supplies from each other, all in real-time while the surgery is being performed.

Traditional manual methods for tracking such supply usage, such as visually identifying the supplies that are used and writing down the type and quantity of such supplies on paper or manually recording such supplies in a database, tend to be slow, tedious, and error-prone. Furthermore, optical scanning technology, such as direct part marking using barcodes on the supplies, has proven to be challenging to implement, due to the nature of the implants. For example, implants often are made of polished stainless steel, are highly reflective, can be very small, have only irregular surfaces (such as the head of a screw), and are subject to a very harsh reprocessing environment (e.g., heat, steam, and chemicals). All of these factors have made it challenging to directly mark implants. It can also be difficult to read such markings under the bright lights of the surgical field during surgery.

Errors in the record of the type and quantity of supplies and implants used can have a variety of negative consequences, including failure of the hospital to be reimbursed for all of the supplies that were used, failure to reorder the correct supplies, lag time in ordering restock supplies in a timely fashion, and errors in the patient's surgical history which can contribute to suboptimal care for the patient in the future.

What is needed, therefore, are improved techniques for tracking the type and quantity of supplies used during surgery.

SUMMARY

A peg, suitable for insertion into a hole in a surgical tray, includes a cap piece, a directional member, and a columnar protrusion. The cap piece includes a machine-readable object that contains data representing information about one or more surgical assets (e.g., screws). The directional member has a directional feature which points in a particular direction and which, when the peg is inserted into the surgical tray, may be oriented to point to one or more surgical assets having the properties represented by the data on the machine-readable object. The columnar protrusion is suitable for being securely inserted into a hole in the surgical tray, such as by being pushed into a hole in a rubber footer, which is commonly used in trays to securely hold implants and other surgical assets and tools. Removal of a surgical asset from the tray is performed by reading data from the machine-readable object that points to the surgical asset and using that data to modify (e.g., decrement or increment) a count of the type of object contained in the tray.

Other features and advantages of various aspects and embodiments of the present invention will become apparent from the following description and from the claims.

DETAILED DESCRIPTION

As described above, the state of the art for recording the use of assets in the surgical field is to perform such recording manually. The surgical technician manually reads the microprinted part numbers on the assets, or on the tray itself next to the corresponding asset. In the case of some assets, such as tightly-packed screws, there is not enough room to print the part numbers on the tray or the caddy. The part numbers are usually written down on a sterile piece of paper, or on the surgical drape itself. This manual process is then followed by a succession of subsequent manual processes, which include multiple manual data entry steps to complete the recording of each removed asset. The entire process if tedious, time-consuming, and error prone.

Embodiments of the preset invention provide an improvement to the process of recording asset usage. In particular, embodiments of the present invention are directed to systems and methods for enabling the use of an asset to be scanned at the time of use, in the field, during surgery. Embodiments of the present invention overcome a problem which has hindered the development of such an improvement, namely that optical scanning technology (e.g., 1D and 2D barcodes) has proven to be problematic to implement on assets and orthopedic trays because: (1) assets are difficult to direct-part mark due to their small size and irregular surfaces; and (2) such surgical assets are subjected to repeated harsh reprocessing environments which expose them to heat, steam, chemicals, and abrasion. As a result, the barcodes tend to get damaged and lose their contrast after multiple exposures to reprocessing.

Furthermore, electronic radio wave technologies, such as RFID, have demonstrated limited capabilities in the surgical field, due to problems such as high cost, large size, signal confusion, and durability.

Short field radio wave microprocessors, such as PharmaSeq's p-Chip, are an example of a chip that may be used within embodiments of the present invention to mark orthopedic assets, such as trays. Such embodiments (referred to as orthopedic tray "mapping") may be used to provide a point of use scanning solution and all of the corresponding benefits to the current manual orthopedic supply chain. Any such solution would be enhanced by providing protection which would shield said chip from the harsh reprocessing environment.

Figure 1A:
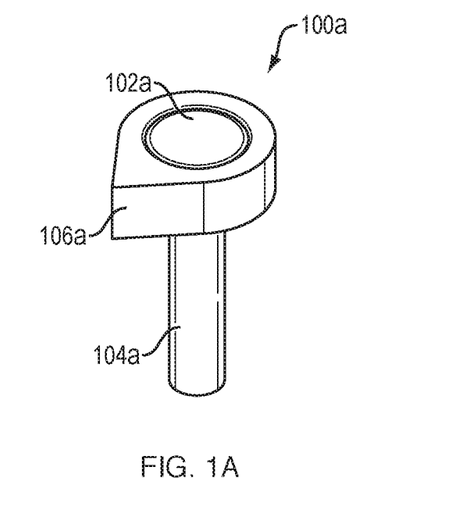
FIGS. 1A and 1B are illustrations of labeled pegs according to embodiments of the present invention.

Referring to FIG. 1A, a labeled peg 100*a* according to one embodiment of the present invention is shown. As will be described in more detail below, the peg 100 may be used to label assets in a surgical tray and to enable a method for recording the use of such assets in the surgical field in real-time. The peg 100*a* includes a cap piece 102*a*. The cap piece 102*a* is or contains a machine-readable object, which may take any of a variety of forms. For example, the machine-readable object may be or include any one or more of the following: a chip, a microprocessor, a non-transitory computer-readable memory, a barcode, or a data matrix code. Regardless of the form that the machine-readable object takes, the machine-readable object may contain data representing information about one or more assets (e.g., screws). The data may, for example, represent any one of more of the following properties of one or more assets: manufacturer, model number, part number, stock keeping unit (SKU), length, and/or width. Those having ordinary skill in the art will understand how to encode such properties in a particular kind of machine-readable object, such as microprocessor, non-transitory computer-readable memory, barcode, or data matrix code.

The cap piece 102*a* may be implemented to have any of a variety of shapes and sizes. For example, in the particular embodiment illustrated in FIG. 1A, the cap piece is in the shape of a disc. The cap piece 102*a* may, however, be in the shape of a wafer (e.g., with a square or rectangular top surface). These are merely examples and do not constitute limitations of the present invention. The cap piece 102*a* may be sufficiently transparent for laser energy to penetrate it to power a chip or other machine-readable object.

Figure 6:
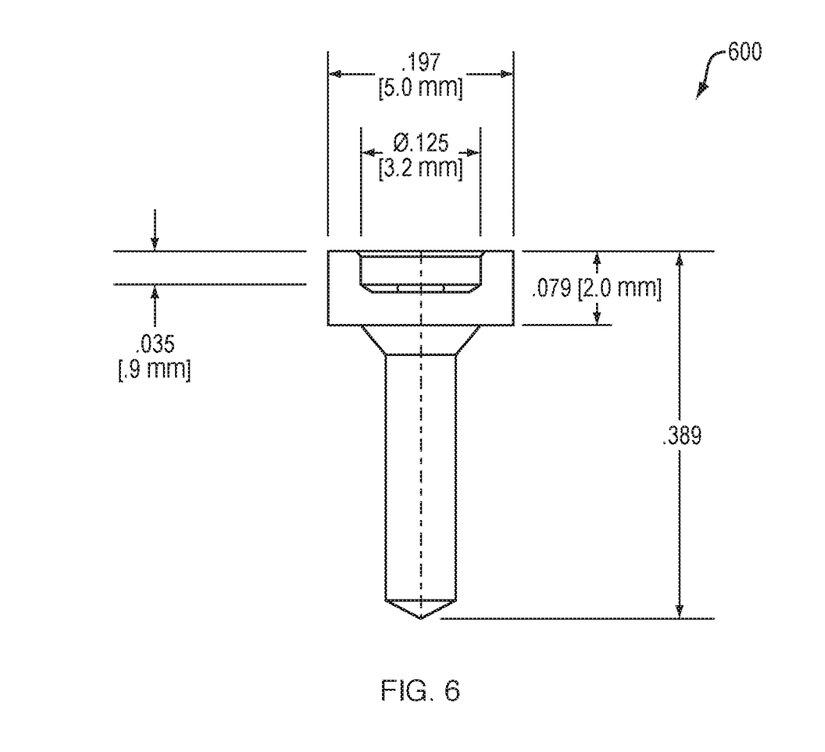
FIG. 6 is a diagram of a side view of one embodiment of the labeled peg of FIG. 1A, drawn to scale.

FIG. 6 shows a side view of one embodiment of the labeled peg 100*a*, drawn to scale. In the particular embodiment of FIG. 6, the cap piece 102 has a diameter of 0.125 in (3.175 mm) and a height (thickness) of 0.35 in (0.9 mm); the circular portion of the directional member 106*a* has a diameter of 0.197 in (5.0 mm) and a height (thickness) of 0.079 in (2.0 mm); and the labeled peg 100*a* has a total height of 0.389 in (9.88 mm).

The cap piece 102*a* may, for example, enclose the machine-readable object. For example, the cap piece 102*a* may include a bottom layer (e.g., disc) and a top layer (e.g., disc), which may sandwich the machine-readable object in between so that the cap piece 102*a* includes the top layer followed by the machine-readable object followed by the bottom layer. The top and/or bottom layer may include a recess into which the machine-readable object may be placed. The recess(es) may have the same shape and a slightly larger size than the machine-readable object, so that the machine-readable object fits snugly within the recess(es).

The top and bottom layers may be secured to each other and thereby enclose the machine-readable object in any of a variety of ways, such as by using a mechanical joining process (e.g., heat staking or ultrasonic welding), thereby securing and protecting the enclosed machine-readable object against the harsh reprocessing environment. The top and/or bottom layers may be made of any material(s), such as a polymer (e.g., polycarbonate).

The peg 100*a* also includes a columnar protrusion 104*a*. The columnar protrusion 104*a* may, for example, be coupled to the bottom of the cap piece 102*a*. The columnar protrusion 104*a* extends downward from the cap piece 102*a* (whether or not coupled to the cap piece). The columnar protrusion 104*a* may, for example, extend in a direction that is perpendicular to the top and/or bottom surface of the cap piece 102*a*. Although the columnar protrusion 104*a* is shown in FIG. 1A as being in the shape of a column (i.e., having a circular cross-section for its entire length), this is merely an example and not a limitation of the present invention. Alternatively, for example, some or all of the length of the columnar protrusion may have a cross-section having a square, rectangular, diamond, or elliptical shape.

As shown in FIG. 1A, the peg 100*a* may also include a directional member 106*a*. The directional member 106*a* has a directional feature, which has a shape that points in a particular direction. In the particular embodiment illustrated in FIG. 1A, the directional feature is a side of the directional member 106*a* which tapers to a point. This, however, is merely an example of the directional feature and not a limitation of the present invention. Alternatively, for example, the directional feature may take the form of, or have a cross section in the shape of, an arrow, a square or cube, a rectangle or rectangular parallelepiped, a cone, or a circle, sphere, or column.

The disc 102*a* may, for example, be coupled to the directional member 106*a*. Such a coupling may be implemented in any of a variety of ways, such as adhesive, heat staking, or ultrasonic welding. As one example, the directional member 106*a* may include a recess into which the disc 102*a* may be placed. The recess may have the same shape and a slightly larger size than the disc 102*a*, so that the disc 102*a* fits snugly within the recess.

In such embodiments, the directional member 106*a* may have a solid bottom surface to which the top of the columnar protrusion 104*a* is coupled. In other embodiments, the top of the columnar protrusion 104*a* may be coupled to the bottom of the disc 102*a*, and the columnar protrusion 104*a* (with the disc 102*a* coupled to its top end) may extend through a gap in the directional member 106*a*. The top surface of the disc 102*a* may be aligned with the top surface of the directional member 106*a*. In such embodiments, the columnar protrusion 104*a* may be fixed in place inside the gap in the directional member 106*a* in any of a variety of ways.

In yet other embodiments, the directional member 106*a* may be integrally formed with the columnar protrusion 104*a*, such as from a single material.

Figure 1B:
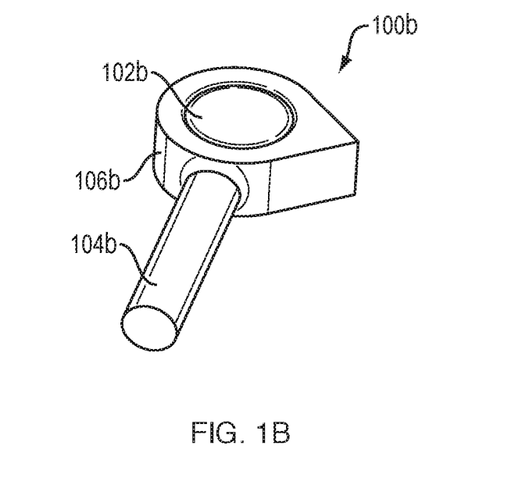

In the embodiment shown in FIG. 1A, the directional member 106*a* points in a direction that is perpendicular to the length of the columnar protrusion 104*a*, and the width (i.e., plane) of the disc 102*a* is perpendicular to the length of the columnar protrusion 104*a*. This is merely one example and does not constitute a limitation of the present invention. An alternative embodiment of a peg 100*b* is shown in FIG. 1B, which includes a disc 102*b* that may be implemented in the same manner as the disc 102*a*, and which includes a columnar protrusion 104*b* that may be implemented in the same manner as the columnar protrusion 104*b*. In the peg 100*b* of FIG. 1B, however, the directional member 106*b* still points in a direction that is perpendicular to the length of the columnar protrusion 104*b*, but the width (i.e., plane) of the disc 102*a* is parallel to the length directional member 106*b*. The different embodiments 100*a* and 100*b* shown in FIGS. 1A and 1B, respectively, may be useful in different applications, depending, for example, on the wide variety of footer layouts that exist in the many orthopedic trays currently in use.

Either of the columnar protrusions 104*a*-*b* may be designed to push into a hole that has been predrilled into a footer (which is typically, but not necessarily, made of silicon rubber) in the surgical tray. As another example, either of the columnar protrusions 104a-b may be designed to push into a corresponding hole in the rubber footer so that the disc 102a or 102b would sit flush with the corresponding surface of the footer.

Figure 2:
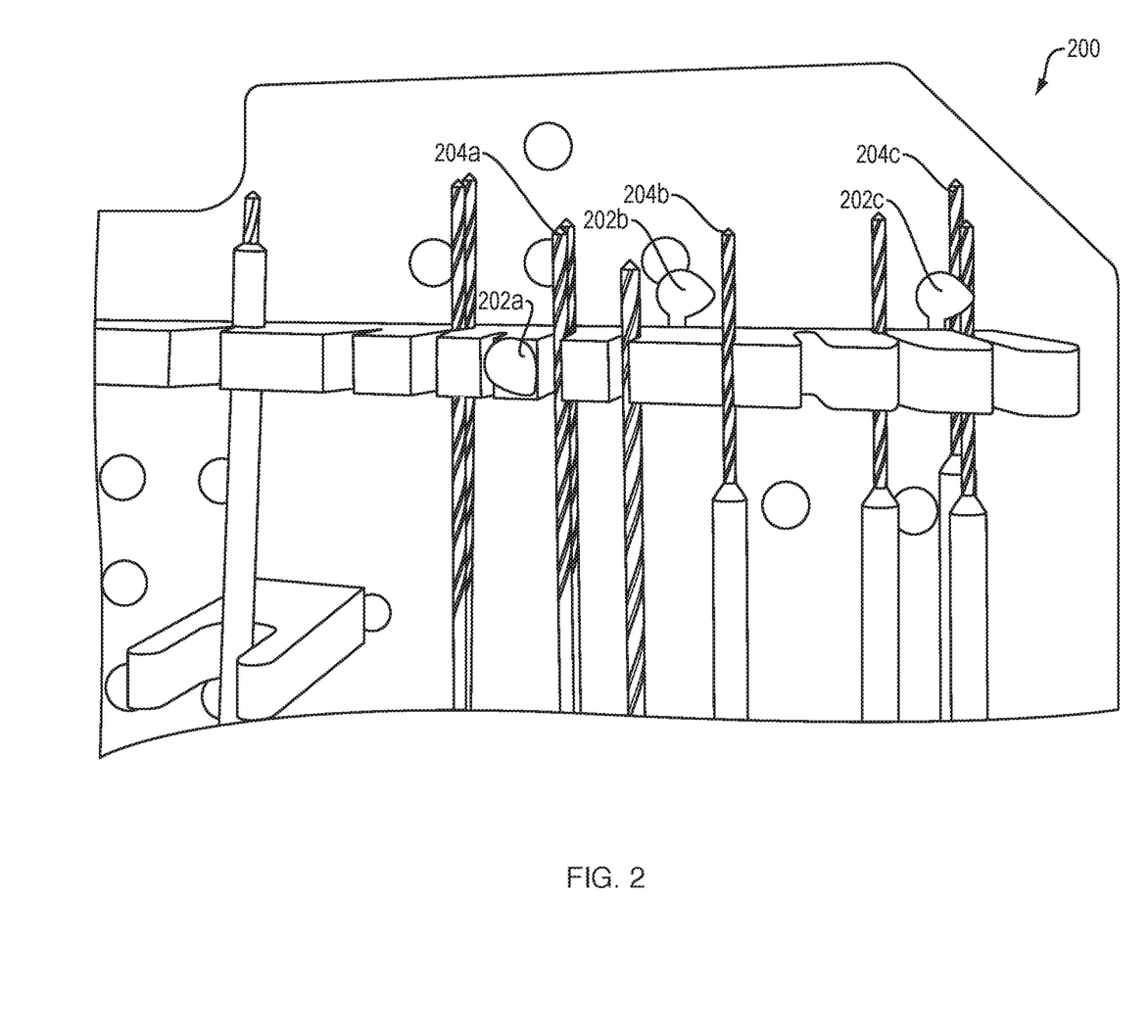
FIG. 2 is an illustration of a surgical tray with a plurality of pegs inserted into it according to an embodiment of the present invention.

Referring to FIG. 2, an illustration is shown of a surgical tray 200 with a plurality of pegs 202a-c inserted into it. The pegs 202a-c may be implemented in any of a variety of ways disclosed herein. The particular number, type, and location of the pegs 202a-c shown in FIG. 2 is merely an example and does not constitute a limitation of the present invention. In the particular example shown in FIG. 2:

A first peg 202a is inserted into a first hole in the tray 200, and points to a first surgical asset (e.g., drill bit) 204a. The first peg 202a includes a machine-readable object which contains data representing one or more features of the first surgical asset 204a.

A second peg 202b is inserted into a second hole in the tray 200, and points to a second surgical asset (e.g., drill bit) 204b. The second peg 202b includes a machine-readable object which contains data representing one or more features of the second surgical asset 204b.

A third peg 202c is inserted into a third hole in the tray 200, and points to a third surgical asset (e.g., drill bit) 204c. The third peg 202c includes a machine-readable object which contains data representing one or more features of the third drill bit 204c.

Figure 3A:
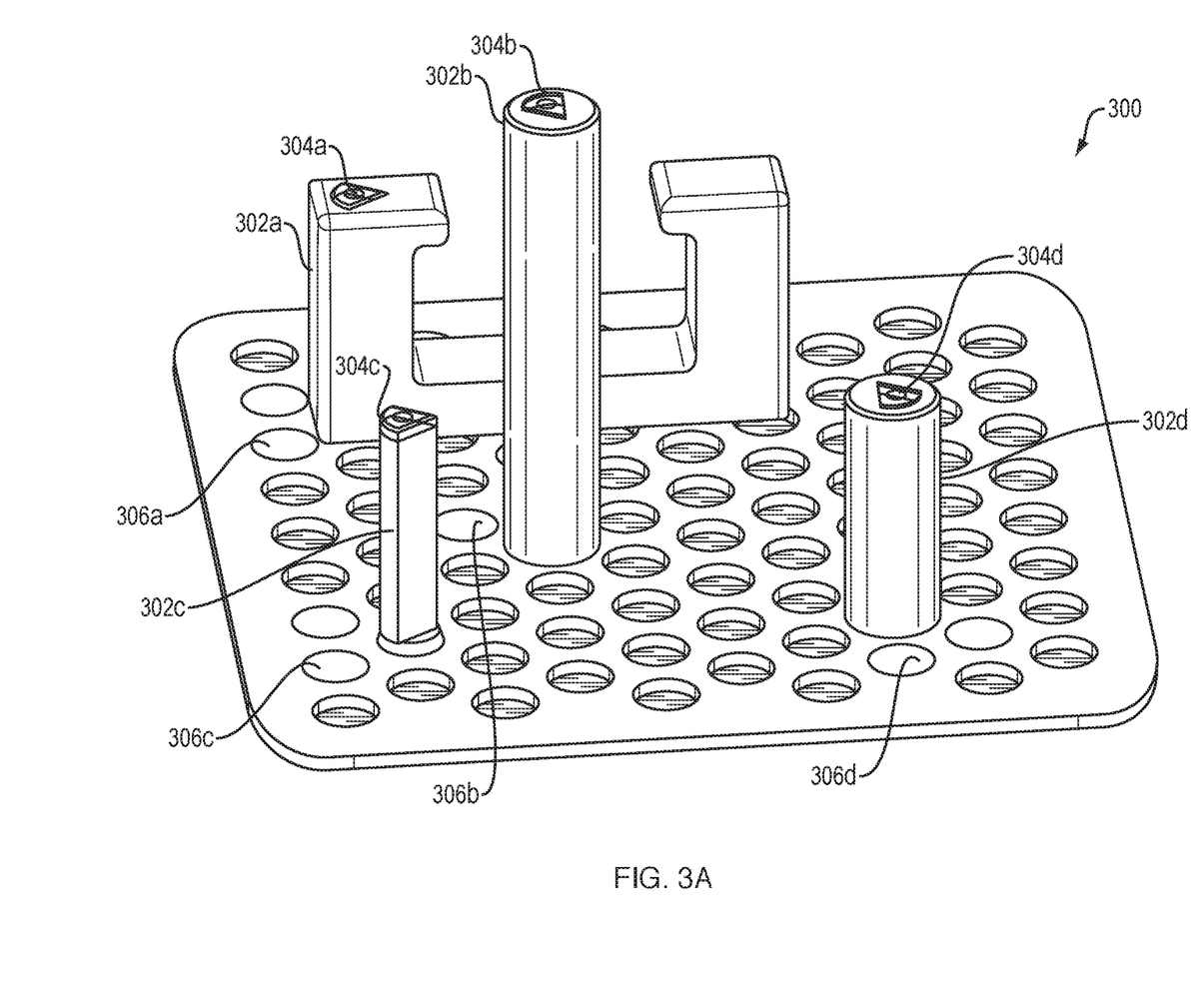
FIGS. 3A-3D are illustrations of various views of a surgical tray with pegs inserted into it according to an embodiment of the present invention.
Figure 3B:
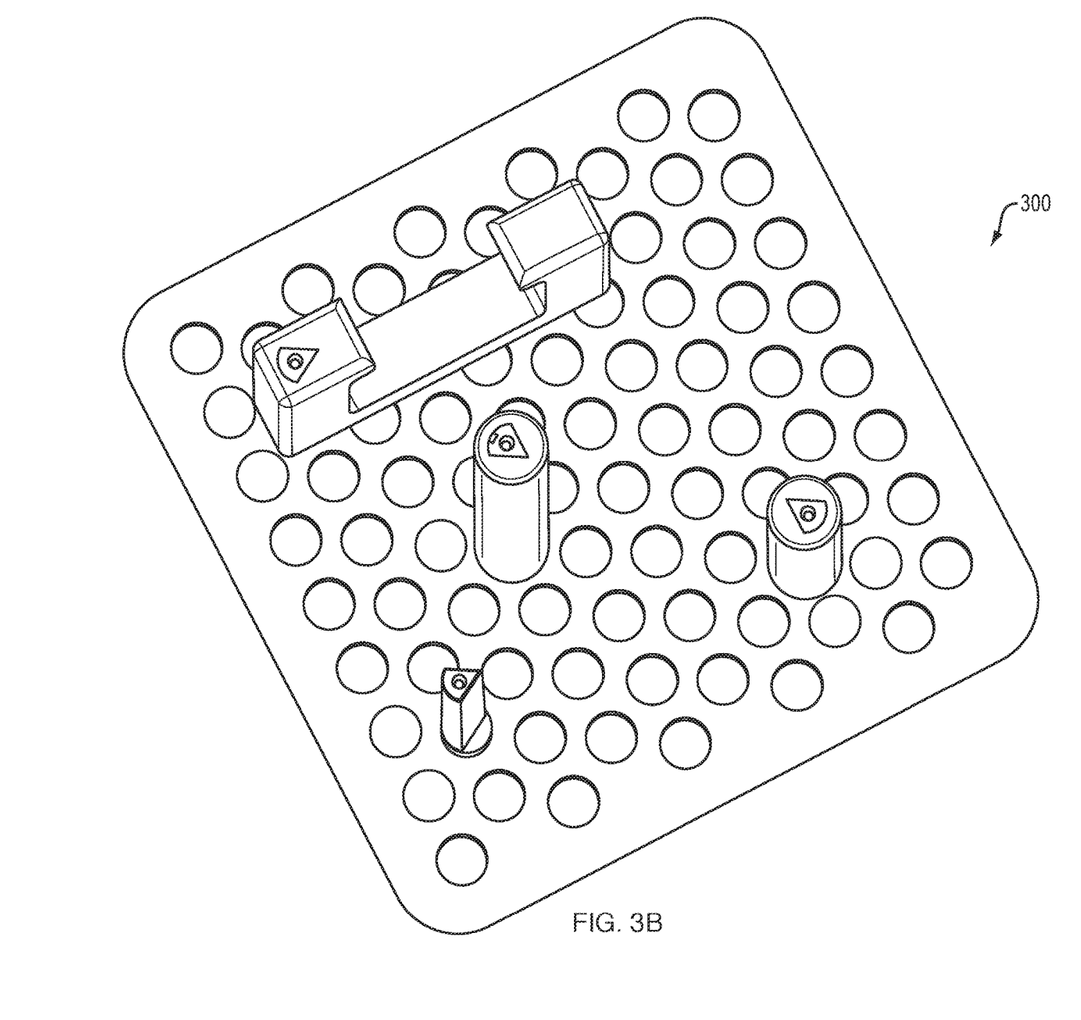

Referring to FIGS. 3A and 3B, a surgical tray 300 is shown with various pegs 302a-302d, implemented according to embodiments of the present invention, inserted into it. FIG. 3A shows the tray 300 in top perspective view, while FIG. 3B shows the tray 300 in top view. More specifically:

The first peg 302a spans several holes in the tray. The first peg 302a contains a directional member 304a, which points towards an interior portion of the peg 302a. The peg 302a is a claw-type peg, which is suitable for holding a plate implant, such that the directional member 304a points to the plate implant when held by the peg 302a. The directional member 304a occupies only a subset of the area of the portion of the peg into which the directional member 304a is inserted.

The second peg 302b is inserted into a single hole and is relatively tall (long), thereby making its directional member 304b easy to read. The directional member 304b points roughly southeast in FIG. 3A, and may thereby be interpreted to point to a single surgical asset (not shown) inserted directly to the southeast of the peg 302b, or to a plurality of surgical assets in the southeasterly direction of the peg 302b.

A third peg 302c has a cross section in the shape of a pie wedge, which is the same shape as its directional member 304c, which points due east in FIG. 3A. The directional member is affixed to (or is snapped on top of) the columnar member of the peg 302c and covers the entire top surface of the peg 302c.

A fourth peg 302d generally has the same structure as the second peg 302b, except that it is shorter. The directional member 304d of the fourth peg 302d points northwest in FIG. 3A.

Figure 3C:
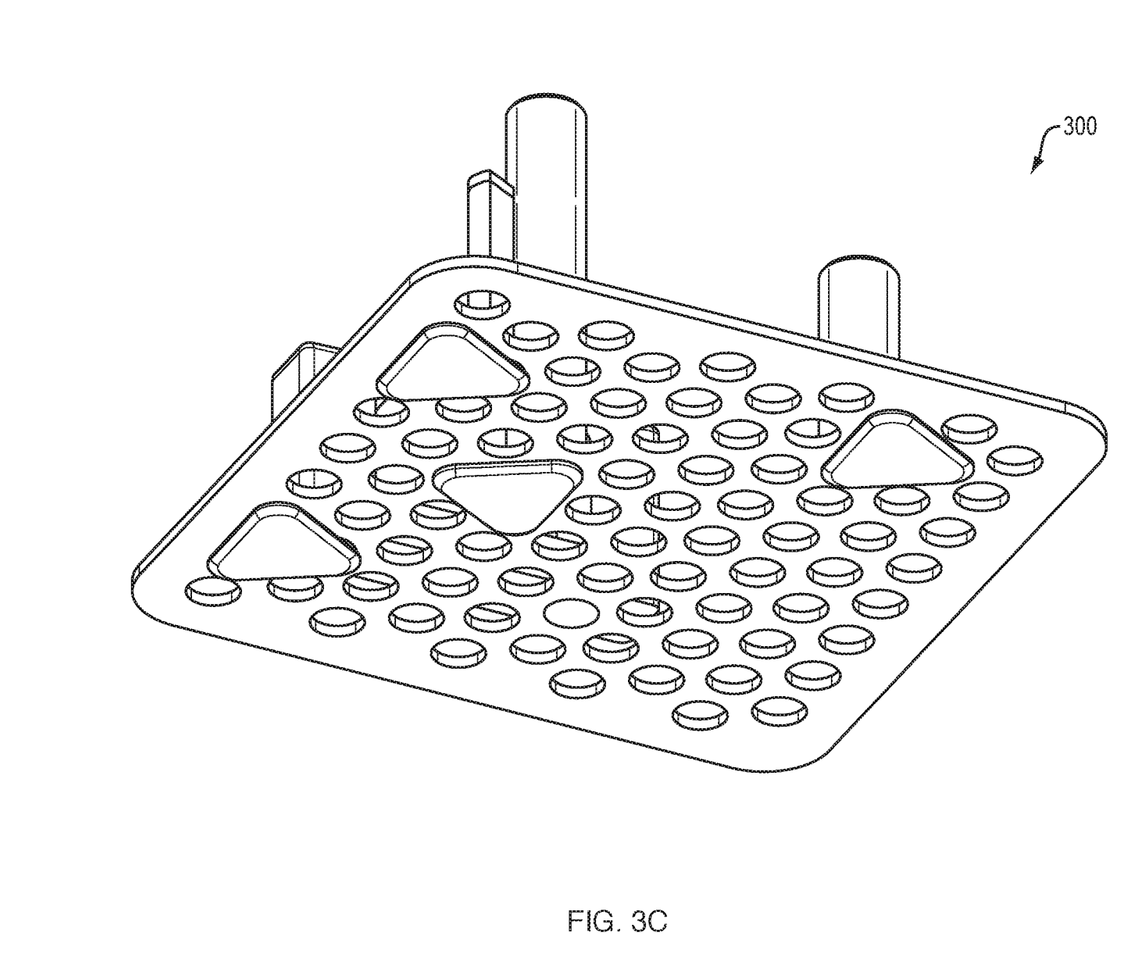
Figure 3D:
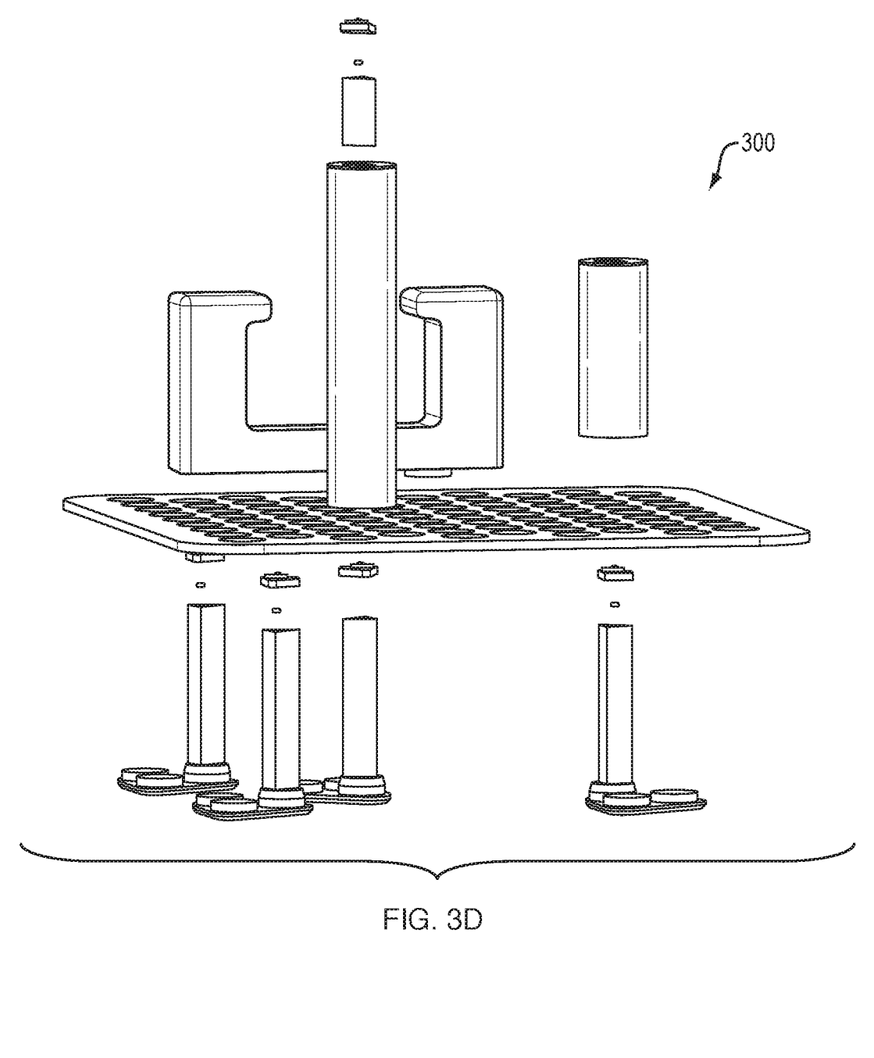

The pegs 302a-c are inserted into corresponding footers 306a-d, respectively, in order to secure the pegs 302a-d into the tray 300, although this is not a requirement of the present invention. This may be seen more clearly in FIG. 3C, which shows the tray 300 in bottom perspective view. As shown therein, the footers 306a-d may be used to secure the pegs 302a-d securely into the tray 300. The exploded view of FIG. 3D shows the full lengths of the footers 306a-d, which may be partially inserted into the columnar protrusions of the pegs 302a-d, respectively.

Figure 4:
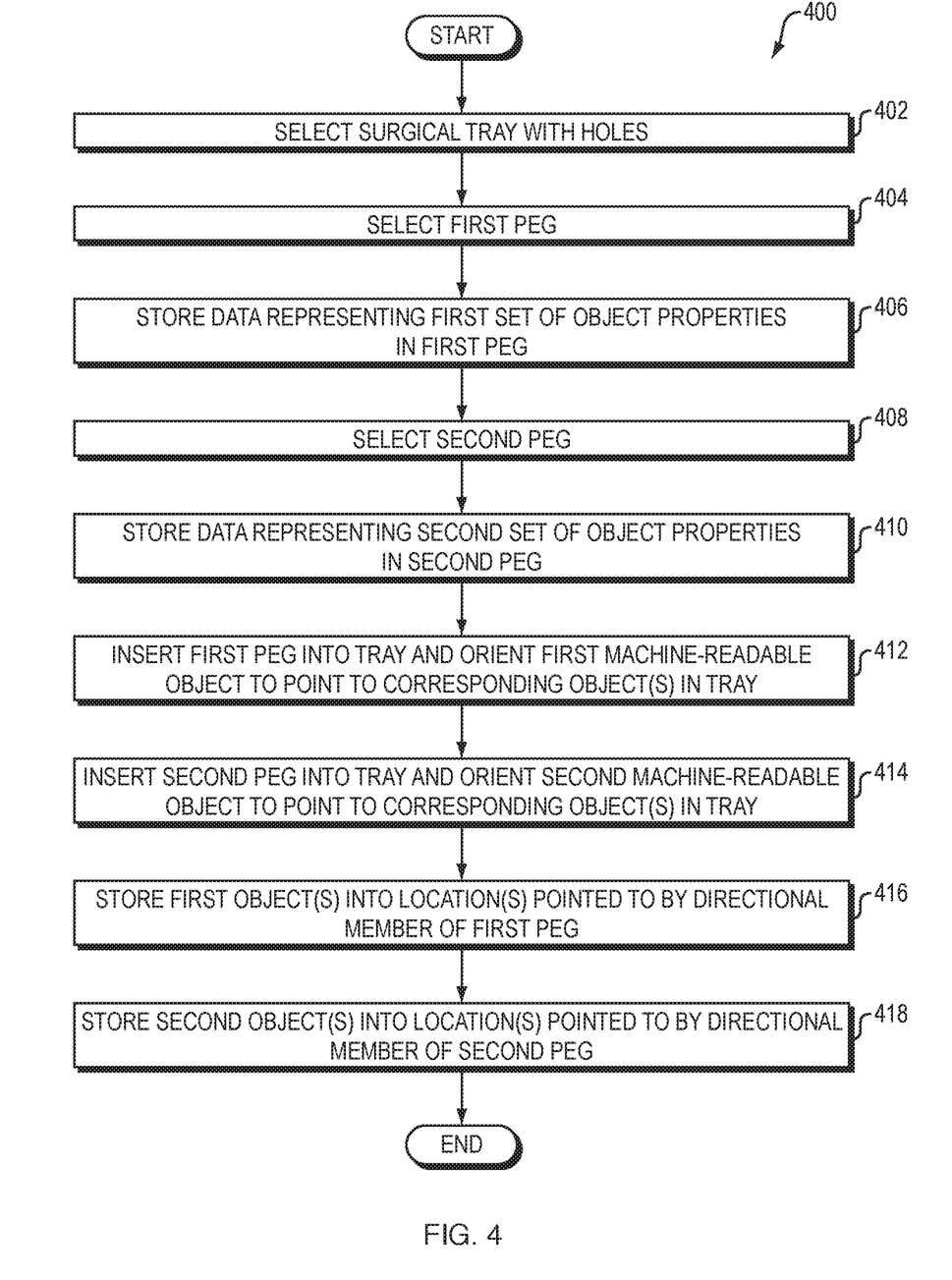
FIG. 4 is a flowchart of a method performed by one embodiment of the present invention to track the removal of objects from a surgical tray.

One embodiment of the present invention is directed to a method for configuring a surgical plating tray using pegs implemented according to embodiments of the present invention, such as pegs of any of the kinds illustrated in FIGS. 1A-1B, 2, and 3A-3D. Referring to FIG. 4, a flowchart is shown of such a method 400 according to one embodiment of the present invention. The method 400 includes selecting a tray having a plurality of holes suitable for containing surgical implements and/or pegs implemented according to embodiments of the present invention (FIG. 4, operation 402). A first set of object properties is identified, such as a set of properties of a first kind of object (e.g., screw). The terms "supply" and "object" are used interchangeably herein. Examples of objects, as that term is used herein, are surgical assets, such as implants, tools, instruments, and one-time use non-implantable objects, such as k-wires, drill bits, and templates. The first set of properties may include any one or more of the kinds of properties described above. A first peg implemented according to an embodiment of the present invention, such as any of the pegs disclosed herein, is selected (FIG. 4, operation 404), and data representing some or all of the first set of object properties is stored in a first machine-readable object in the first peg (FIG. 4, operation 406).

A second set of object properties is identified, such as a set of properties of a second kind of object (e.g., screw). The second set of properties may include any one or more of the kinds of properties described above. The second set of properties may differ from the first set of properties in whole or in part. For example, the second set of properties may include a SKU or length that differs from the SKU or length of the first set of properties. A second peg implemented according to an embodiment of the present invention, such as any of the pegs disclosed herein, is selected (FIG. 4, operation 408), and data representing some or all of the second set of object properties is stored in a second machine-readable object in the second peg (FIG. 4, operation 410).

Note that operations 408 and 410 effectively repeat operations 404 and 406, but for a second peg and second machine-readable object. Operations 404 and 406 may be repeated for any additional number of pegs and corresponding machine-readable objects.

The first peg is inserted into the tray in a first hole, and the directional member of the first peg is oriented (e.g., rotated) so that it points towards a location or locations in the tray in which one or more objects (e.g., screws) are stored, or will be stored, where such object(s) have some or all of the properties stored in the data of the first peg's machine-readable object (FIG. 4, operation 412). Similarly, the second peg is inserted into the tray in a second hole, and the directional member of the second peg is oriented (e.g., rotated) so that it points towards a location or locations in the tray in which one or more objects (e.g., screws) are stored, or will be stored, where such object(s) have some or all of the properties stored in the data of the second peg's machine-readable object (FIG. 4, operation 414). Note that operation 414 effectively repeats operation 414, but for a second peg. Operation 414 may be repeated for any additional number of pegs. Furthermore, any of the pegs may be inserted into more than one hole in the tray (as in the example of the peg 302a in FIG. 3A).

One or more objects (e.g., screws) of the type represented by the data in the machine-readable object of the first peg are inserted into the location(s) pointed to by the directional member of the first peg (FIG. 4, operation 416). One or more objects (e.g., screws) of the type represented by the data in the machine-readable object of the second peg are inserted into the location(s) pointed to by the directional member of the second peg (FIG. 4, operation 418). Note that operation 418 effectively repeats operation 418, but for a second peg and corresponding type of object. Operation 418 may be repeated for any additional number of pegs and corresponding types of objects.

The result of performing method 400 is to populate a tray, such as the tray shown in FIGS. 3A-3D, with pegs and corresponding objects (e.g., screws) which are pointed to by the pegs and which have properties represented by the data in the machine-readable objects of the pegs that point to those objects. As will be described in more detail below in connection with FIG. 5, this enables the removal of such objects from the tray to be detected.

The order of the steps shown in FIG. 4 is merely an example and does not constitute a limitation of the present invention. The steps of method 400 may be performed in orders other than the order shown in FIG. 4. For example, steps 416 and 418 may be performed before steps 412 and 414. As another example, steps 406, 406, 408, and 410 may be performed after steps 416 and 418.

Embodiments of the present invention include methods for reading data from machine-readable objects (such as the machine-readable objects in cap pieces 102a-b in FIGS. 1A-1B) to track the removal of objects (e.g., surgical assets) from a surgical tray. For example, referring to FIG. 5, a flowchart is shown of a method 500 for tracking the removal of objects from a tray according to one embodiment of the present invention.

Figure 5:
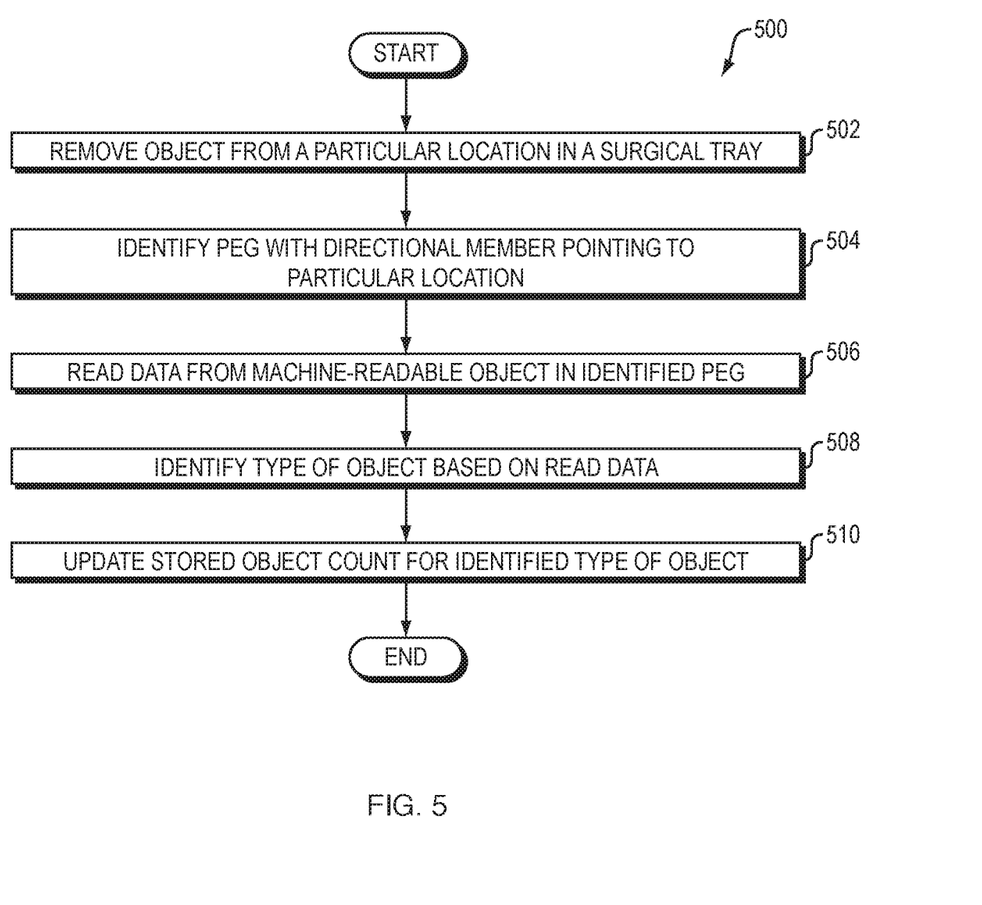
FIG. 5 is a flowchart of a method for tracking the removal of objects from a tray according to one embodiment of the present invention.

An object (e.g., screw) is removed from a particular location (e.g., hole) of the tray (FIG. 5, operation 502). A peg having a directional member that points to the particular location of the tray is identified (FIG. 5, operation 504). For example, if drill bit 204a were removed from the tray 200 in FIG. 2, then peg 202a may be identified, because the directional member of the peg 202a points to the location in the tray in which the drill bit 204a is or was stored. In some embodiments of the present invention, a human operator identifies the peg having a directional member that points to the particular location of the tray by visual inspection of the tray and the pegs and objects that it contains.

As described above, a peg may point to more than one object. As this implies, if the method 500 is repeated in connection with the removal of multiple objects from the tray, then the same peg may be identified as pointing to those multiple objects.

One or more units of data are read from a machine-readable object contained within the identified peg (FIG. 5, operation 506). Such data may be read in any of a variety of ways. For example, a wand may be positioned (e.g., by a human operator) over the surface of the machine-readable object, thereby causing the wand to read some or all of the data from the machine-readable object. The wand or other reading device may be triggered to read data from the machine-readable object in response to input from the human operator, such as the pressing of a button.

A computer (not shown) may automatically identify the type (e.g., length) of the removed object based on the data read from the machine-readable object (FIG. 4, operation 408). For example, if the data read from the machine-readable object include data which expressly specifies a type of the removed object, then the computer may identify the type of the removed object as the type expressly specified by the read data. As another example, the computer may derive the type of the removed object from the data read from the machine-readable object. For example, if the data read from the machine-readable object specifies a length of the removed object, then the computer may derive the type of the removed object from the specified length, such as by using a table or other data structure to correlate the specified length with an object type (e.g., part number or SKU).

The method 500 decrements a stored count of the identified object type (FIG. 5, operation 510). For example, the computer may include a database or other data structure containing counts of various types of objects. As a particular example, such a data structure may begin with a count, for each of the object types initially stored in the tray, of the number of objects of that type initially stored in the tray. Such a data structure may include, for each of one or more objects, additional data about that object, such as its part number and a unique identifier of the object, such as a unique identifier that is stored in the object's machine-readable object.

In addition to or instead of decrementing the stored count of the identified object type, the method 500 may increment a count of the number of objects of the identified object type that have been removed from the tray. For example, the computer may initially contain data indicating that zero objects of each object type have been removed from the tray, such as when the method 400 of FIG. 4 is performed to initially load the tray. Then, as each object is removed from the tray, the method 500 may increment a count of the number of objects of that type that have been removed from the tray.

Operations 502-510 may be repeated for any number of objects removed from the tray. The function performed by the method 500 is to maintain an accurate count of the number of objects removed from the tray.

Embodiments of the present invention have a variety of advantages. For example, by enabling the removal of objects (e.g., screws) from the tray to be tracked by reading machine-readable data from machine-readable objects in the tray, and thereby automatically updating a count of such removed objects in a computer, embodiments of the present invention decrease the effort, increase the speed, and increase the accuracy of such tracking in comparison to prior art object removal tracking methods. In particular, embodiments of the present invention eliminate the need for any human operator to write down or manually enter data specifying the objects removed from the tray. This significantly decreases the complexity of the tracking process and enables such tracking to be performed nearly instantly after an object has been removed from the tray.

Other industries, and even departments within hospitals other than the surgical department, consider scanning at the point of use to be the gold standard for supply chain accuracy and management because of the wide range of benefits that it provides. Embodiments of the present invention enable such scanning at the point of use, by employing a combination of novel and nonobvious technical means to enable screws and other supplies to be scanned during surgical procedures in the sterile field at the time at which such supplies are used. Embodiments of the present invention take all of the advantages of scanning at the point of use and apply them to the surgical context.

Embodiments of the present invention have a variety of benefits over existing systems which use tape that is affixed to a surface of the surgical tray to identify objects in the tray. For example, tape typically has a shorter lifecycle than embodiments of the present invention. Furthermore, pegs implemented according to embodiments of the present invention may be constructed to provide better protection to the machine-readable object (e.g., chip) than tape, such as by covering the machine-readable object with polycarbonate. Yet another advantage of embodiments of the present invention over tape is that pegs which have been inserted into tray holes are more easily removed and replaced than tape which has been affixed to the surface of the tray.

Another benefit of embodiments of the present invention is that, because they can be inserted into holes in existing surgical trays, they can be used in connection with the large number and wide variety of surgical trays currently in use. Over 200,000 surgical trays currently are in use in the U.S. alone, so the ability to use pegs implemented according to embodiments of the present invention presents the opportunity to use such pegs in a large number of existing trays, rather than requiring new trays to be designed and constructed.

The ability to insert pegs into the holes of existing surgical trays provides yet another benefit over the use of tape, namely that tape can only be affixed to a surface of the surgical tray. This makes tape of limited use with surgical trays that are covered densely in holes, and in which surface area, therefore, is limited. In contrast, as the number of holes in a tray increases and the amount of surface area decreases, the number of opportunities for inserting pegs into the surgical tray increases, while the number of opportunities for affixing tape to the surface of the surgical tray decreases.

Yet another benefit of pegs implemented according to embodiments of the present invention in comparison to tape is that it can be difficult to read the surface of a piece of tape if tall objects have been densely packed into the tray, because there may be little space between such objects into which to insert the wand. In contrast, even if a tray is densely packed with pegs, the machine-readable objects in such pegs may easily be read with a wand because the wand need only be moved to the top of such pegs.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more machines, such as computers, computer processors, and/or other elements of a computer system. Such features are either impossible or impractical to implement mentally and/or manually. For example, embodiments of the present invention read data from a machine-readable object, such as by using a wand to read data from a chip. This function cannot be performed by a human manually or mentally.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic discs such as internal hard discs and removable discs; magneto-optical discs; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disc (not shown) or a removable disc. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. An asset tray comprising:
 a plurality of holes;
 a first peg, comprising a first directional member and a first machine-readable object, in a first hole in the plurality of holes,
  the first machine-readable object including a first non-transitory machine-readable storage medium containing first data representing a first property of at least one first supply,
  the first directional member pointing to a second hole in the plurality of holes;
 a first supply in the second hole in the plurality of holes, wherein the first supply has the first property.

2. The asset tray of claim 1, wherein the first peg further comprises a columnar protrusion that is inserted into the first hole in the plurality of holes.

3. The asset tray of claim 1, wherein the first supply comprises a first screw.

4. The asset tray of claim 1, further comprising:
 a second peg, comprising a second directional member and a second machine-readable object, in a third hole in the plurality of holes,
  the second machine-readable object including a second non-transitory machine-readable storage medium containing second data representing a second property of at least one second supply;
  the second directional member pointing to a fourth hole in the plurality of holes;
 a second supply in the fourth hole in the plurality of holes, wherein the second supply has the second property;
 wherein the first property differs from the second property.

5. The asset tray of claim 4, wherein the first property comprises a length of the first supply, wherein the second property comprises a length of the second supply, and wherein the first length differs from the second length.

6. The asset tray of claim 1, wherein the first non-transitory machine-readable storage medium comprises a non-transitory computer-readable memory.

7. The asset tray of claim 1, wherein the first non-transitory machine-readable storage medium comprises a barcode.

8. The asset tray of claim 1, wherein the first non-transitory machine-readable storage medium comprises a data matrix code.

9. A method for use with an asset tray, the asset tray comprising:
 a plurality of holes;
 a first peg, comprising a first directional member and a first machine-readable object, in a first hole in the plurality of holes, the first machine-readable object including a first non-transitory machine-readable storage medium containing first data representing a first property of at least one first supply, the first directional member pointing in a direction of a second hole in the plurality of holes; and
 a first supply in the first hole in the plurality of holes, wherein the first supply has the first property;
 the method comprising:
  (1) reading the first data from the first non-transitory machine-readable storage medium;
  (2) identifying the first supply based on the direction of the first directional member;
  (3) identifying a type of the first supply based on the first data read from the first non-transitory machine-readable storage medium; and
  (4) updating a stored count of the type of the first supply.

10. The method of claim 9, wherein the first machine-readable object comprises a non-transitory computer-readable memory.

11. The method of claim 9, wherein the first supply comprises a screw.

12. The method of claim 9, wherein (4) comprises incrementing the stored count of the type of the first supply.

13. The method of claim 9, wherein (4) comprises decrementing the stored count of the type of the first supply.

14. The method of claim 9, wherein the type of the first supply comprises a length of the first supply.

15. The method of claim 9, wherein (1) comprises reading the first data using a wand.

16. The method of claim 9, further comprising removing the first supply from the tray before (1).

* * * * *